United States Patent [19]
Dionne et al.

[11] Patent Number: 6,132,420
[45] Date of Patent: *Oct. 17, 2000

[54] OSMOTIC DELIVERY SYSTEM AND METHOD FOR ENHANCING START-UP AND PERFORMANCE OF OSMOTIC DELIVERY SYSTEMS

[75] Inventors: Keith E. Dionne, Cambridge, Mass.; Scott D. Lautenbach, San Mateo, Calif.

[73] Assignee: Alza Corporation, Mountain View, Calif.

[*] Notice: This patent is subject to a terminal disclaimer.

[21] Appl. No.: 08/970,530

[22] Filed: Nov. 14, 1997

Related U.S. Application Data

[63] Continuation-in-part of application No. 08/943,007, Oct. 2, 1997, Pat. No. 5,985,305, which is a continuation of application No. 08/791,699, Jan. 30, 1997, Pat. No. 5,728,396, which is a continuation-in-part of application No. 08/595,761, Feb. 2, 1996, abandoned.
[60] Provisional application No. 60/030,481, Nov. 15, 1996.

[51] Int. Cl.⁷ ....................................................... A61K 9/22
[52] U.S. Cl. ...................................... 604/892.1; 424/422
[58] Field of Search ................................. 424/473, 467, 424/472, 438, 452, 422; 604/892.1, 890.1, 143

[56] References Cited

U.S. PATENT DOCUMENTS

| | | |
|---|---|---|
| 3,797,492 | 3/1974 | Place . |
| 3,987,790 | 10/1976 | Eckenhoff et al. . |
| 4,008,719 | 2/1977 | Theeuwes et al. . |
| 4,865,845 | 9/1989 | Eckenhoff et al. . |
| 4,915,954 | 4/1990 | Ayer et al. . |
| 5,057,318 | 10/1991 | Magruder et al. . |
| 5,059,423 | 10/1991 | Magruder et al. . |
| 5,112,614 | 5/1992 | Magruder et al. . |
| 5,137,727 | 8/1992 | Eckenhoff . |
| 5,151,093 | 9/1992 | Theeuwes et al. . |
| 5,209,746 | 5/1993 | Balaban et al. . |
| 5,234,692 | 8/1993 | Magruder et al. . |
| 5,234,693 | 8/1993 | Magruder et al. . |
| 5,234,695 | 8/1993 | Hobbs et al. . |
| 5,279,608 | 1/1994 | Cherif Cheikh . |
| 5,308,348 | 5/1994 | Balaban et al. . |
| 5,318,558 | 6/1994 | Linkwitz et al. . |
| 5,320,616 | 6/1994 | Magndu et al. ..................... 604/892.1 |
| 5,336,057 | 8/1994 | Fukuda et al. . |
| 5,456,679 | 10/1995 | Balaban et al. . |
| 5,728,396 | 3/1998 | Peery et al. ............................. 424/422 |
| 5,795,591 | 8/1998 | Lee et al. ................................ 424/473 |
| 5,830,501 | 11/1998 | Dong et al. ............................. 424/473 |

FOREIGN PATENT DOCUMENTS 0373867 6/1990 European Pat. Off. .

OTHER PUBLICATIONS

E.L.P. Uhlig, W.F. Graydon and Dr. W. Zingg—"The electro–osmotic acutation of implantable insulin micropumps," Journal of Biomedical Materials Research, vol. 17, 931–943 (1983).

G. Luft, D. Kuehl and G.J. Richter— "Electro–osmotic valve for the controlled administration of drugs," Medical & Biological Engineering & Computing, 45–50 (Jan. 1978).

*Primary Examiner*—Mark O. Polutta
*Assistant Examiner*—Kelly M Cheney
*Attorney, Agent, or Firm*—Steve Stone; Pauline Ann Clarke

[57] ABSTRACT

The present invention relates to an osmotically driven agent delivery system for delivering a beneficial agent. The osmotic delivery system includes an osmotic agent which operates by imbibing fluid from an outside environment, causing the release of a beneficial agent. The osmotic delivery system includes a liquid or gel additive surrounding the osmotic agent for enhancing start-up and lubricating the osmotic agent. The liquid or gel additive is an incompressible lubricating fluid which fills any air gaps between the osmotic agent and the walls of a chamber and substantially reduces start-up delays.

23 Claims, 3 Drawing Sheets

OSMOTIC DELIVERY SYSTEM AND METHOD FOR ENHANCING START-UP AND PERFORMANCE OF OSMOTIC DELIVERY SYSTEMS

CROSS REFERENCE TO RELATED APPLICATIONS

This application is a continuation-in-part application of U.S. application Ser. No. 08/943,007, filed Oct. 2, 1997, now U.S. Pat. No. 5,985,305, which is a continuation application of U.S. application Ser. No. 08/791,699, filed Jan. 30, 1997 (now U.S. Pat. No. 5,728,396), which is a continuation-in-part of U.S. application Ser. No. 08/595,761, filed Feb. 2, 1996 (now abandoned).

This application also claims the benefit of U.S. Provisional Application Ser. No. 60/030,481, filed Nov. 15, 1996, pursuant to 35 U.S.C. § 119(e).

BACKGROUND

1. Field of the Invention

The present invention relates to a delivery device for delivery of beneficial agents at a controlled rate, and more particularly, the invention relates to osmotic drug delivery systems and methods for enhanced start-up and performance of osmotic drug delivery systems.

2. Description of the Related Art

Controlled delivery of beneficial agents, such as drugs, in the medical and veterinary fields has been accomplished by a variety of methods. One method for controlled and prolonged delivery of beneficial agents involves the use of osmotic delivery systems. These devices can be implanted to release the beneficial agent in a controlled manner over a preselected time or administration period. In general, osmotic delivery systems operate by imbibing fluid from the outside environment and releasing corresponding amounts of the beneficial agent.

Osmotic delivery systems, commonly referred to as "osmotic pumps," generally include some type of a capsule having walls which selectively pass water into an interior of the capsule which contains a water-attracting osmotic agent. The absorption of water by the water-attracting agent within the capsule reservoir creates osmotic pressure within the capsule which causes the beneficial agent to be delivered from the capsule. The water-attracting agent may be the beneficial agent delivered to the patient; however, in most cases, a separate osmotic agent is used specifically for its ability to draw water into the capsule.

When a separate osmotic agent is used, the osmotic agent may be separated from the beneficial agent within the capsule by a movable dividing member or piston. The structure of the capsule is such that the capsule does not expand when the osmotic agent takes in water. As the osmotic agent expands, it causes the beneficial agent to be discharged through an orifice at the same rate as the water enters the osmotic agent by osmosis. Osmotic delivery systems may be designed to deliver a beneficial agent at a controlled constant rate, a varying rate, or in a pulsatile manner.

In known osmotic delivery systems, an osmotic tablet is used as the osmotic agent and is placed inside the capsule. The osmotically active agent and the compartment in which it resides may be referred to as an "osmotic engine." A membrane plug is then placed in an opening in the capsule through which the tablet was inserted. The water enters the capsule through the membrane plug. Alternatively, water may enter directly through the capsule walls if they are permeable to water.

Due to machining and tableting tolerances, the osmotic tablet in the solid initial state is generally sized somewhat smaller than the reservoir in which it is received. Thus, there are air-filled gaps between the osmotic tablet and the surrounding walls of the chamber, between the osmotic tablet and the membrane plug through which water is absorbed, and between the osmotic tablet and the piston. Due to these air-filled gaps, when water begins to be drawn into the osmotic tablet though the membrane plug, the osmotic tablet expands into the surrounding air space and beneficial agent delivery start-up is delayed by a time during which the osmotic tablet expands to fill the air spaces within the chamber. The start-up may be delayed up to several days or weeks depending on the size of the air gaps and the flow rate of the system. Delayed start-up of beneficial agent delivery is a significant problem in osmotic delivery systems.

Another potential problem with known osmotic delivery systems is freezing-up or locking of the osmotic tablet against the sides of the chamber. The osmotic tablet passes through several states from the solid initial state to the hydrated delivery state. As the tablet begins to swell upon wetting it acts more like a solid than a deformable gel. Upon initial wetting, the swelling of the tablet can cause it to lock against the rigid capsule reservoir side walls causing the agent delivery to be delayed until sufficient water has permeated into the osmotic tablet to soften the tablet to the point where it flows. The freeze-up of the osmotic tablet upon initial wetting leads to delayed delivery. In addition, freeze-up can also lead to catastrophic problems such as membrane rupture, expulsion of the membrane plug, or a sudden increase in the delivery rate of the beneficial agent.

Known osmotic delivery systems include those disclosed in U.S. Pat. Nos. 3,797,492, 3,987,790, 4,008,719, 4,865,845, 5,057,318, 5,059,423, 5,112,614, 5,137,727, 5,151,093, 5,234,692, 5,234,693, 5,279,608, and 5,336,057. Pulsatile delivery devices are also known which deliver a beneficial agent in a pulsatile manner as disclosed in U.S. Pat. Nos. 5,209,746, 5,308,348, and 5,456,679. The disclosure of each of the above identified patents is hereby incorporated by reference in its entirety to the same extent as if the language of each patent were specifically and individually incorporated by reference.

SUMMARY OF THE INVENTION

The device according to the present invention addresses the disadvantages of the prior art osmotic delivery systems by providing an osmotic engine and method for enhancing start-up and performance of osmotic delivery systems. The osmotic engine reduces start-up delays and prevents freeze-up of the osmotic agent.

According to one aspect of the present invention, an osmotic drug delivery device includes a capsule including a first chamber for containing a beneficial agent and a second chamber containing an osmotic agent, an at least partially fluid permeable wall of the second chamber allowing fluid to pass from a surrounding environment into the second chamber, and an incompressible fluid additive or filler within the second chamber surrounding the osmotic agent.

BRIEF DESCRIPTION OF THE DRAWING FIGURES

The invention will be described in greater detail with reference to the accompanying drawings in which like elements bear like reference numerals, and wherein.

DETAILED DESCRIPTION

The present invention relates to an osmotic drug delivery system for delivering a beneficial agent. The delivery system according to the present invention includes an additive for enhancing start-up and lubricating the osmotic agent.

Figure 1:
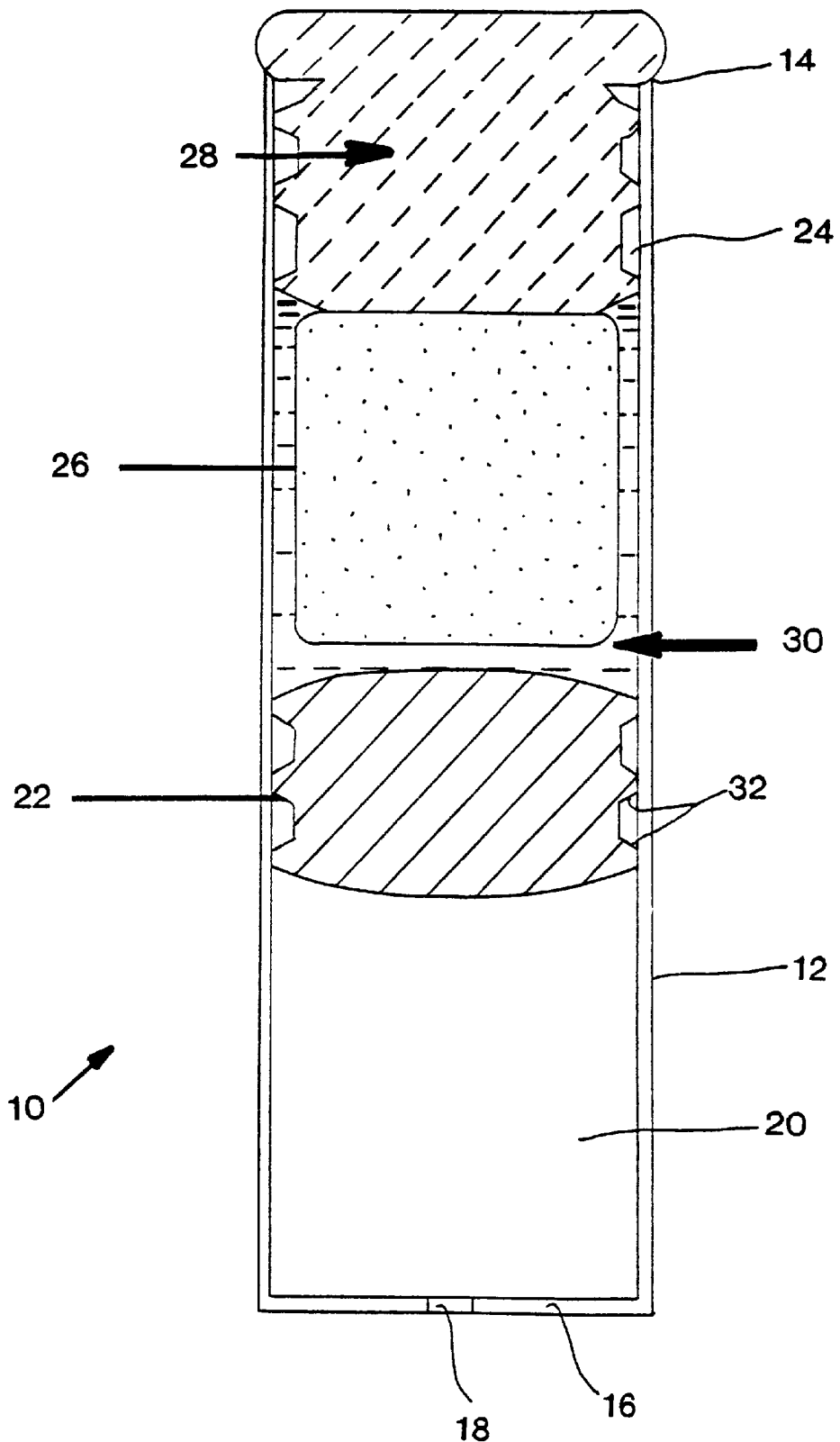
FIG. 1 is a side sectional view of an osmotic delivery device according to the present invention.

FIG. 1 illustrates an example of an osmotic drug delivery device 10 according to the present invention. The configuration illustrated in FIG. 1 is one example of a drug delivery device and is not to be construed as limiting the present invention. The present invention is generally applicable to all osmotic delivery devices having any number of shapes, and to all such devices administered in any variety of methods such as oral, ruminal, and implantable osmotic delivery techniques.

The osmotic drug delivery device 10, as illustrated in FIG. 1, includes an enclosure or elongated substantially cylindrical capsule 12 having a first open end 14, and a second enclosed end 16. The closed end 16 has one or more fluid delivery orifices 18. The elongated capsule 12 is formed of a material which is sufficiently rigid to withstand expansion of an osmotic agent without changing size or shape. The elongated capsule 12 may also be largely impermeable to fluids in the environment as well as to ingredients contained within the dispensing device such that the migration of such materials into or out of the device through the impermeable material is so low as to have substantially no adverse impact on the function of the osmotic delivery device.

Within the capsule 12 is a first chamber 20 for containing a beneficial agent to be delivered. Such a beneficial agent may optionally include pharmaceutically acceptable carriers and/or additional ingredients such as antioxidants, stabilizing agents, permeation enhancers, etc.

The embodiment of the present invention illustrated in FIG. 1 includes a movable partition or piston 22. A second chamber 24 within the capsule 12 is separated from the first chamber 20 by the movable piston 22. The second chamber 24 receives an osmotic agent, which in the embodiment of the present invention depicted in FIG. 1 is one or more osmotic tablets 26. The osmotic tablet is initially non-flowable and solid. Osmotic agents, specifically the osmotic tablet 26 of the embodiment of the present invention illustrated FIG. 1, drive the osmotic flow of osmotic delivery devices. The osmotic agent need not be a tablet; it may be other conceivable shapes, textures, densities, and consistencies and still be within the confines of the present invention. For example, the osmotic agent may be in the form of a powder.

The movable piston 22 is a substantially cylindrically member which is configured to fit within the capsule 12 in a sealed manner which allows the piston to slide along a longitudinal direction within the capsule. The piston 22 may be in the form of a slidable partition or a stationary and stretchable partition member. The piston 22 preferably is formed of an impermeable resilient material and includes annular ring shape protrusions 32 which form a seal with the inner surface of the capsule. However, the present invention need not include the movable piston or partition 22; in such an embodiment, the first chamber 24 and the second chamber 20 are separated by an interface between the osmotic agent 26 and the beneficial agent. Thus, when the osmotic delivery system according to one embodiment of the present invention is in use, the volumes of the first chamber 24 and the second chamber 20 change as the osmotic agent 26 imbibes fluid from the surrounding environment.

As illustrated in FIG. 1, the drug delivery device 10 of one embodiment of the present invention includes a membrane plug 28 which is inserted in the open end 14 of the capsule 12 after placing the osmotic tablet 26 within the capsule. The membrane plug 28 is formed of a semi-permeable material which allows fluid to pass from an exterior fluid environment into the second chamber 24 to cause the osmotic tablet 26 to swell. However, the semipermeable material forming the membrane plug 28 is largely impermeable to the materials within the capsule and other ingredients within the fluid environment.

The osmotic delivery device according to the present invention includes an incompressible additive or filler within the second chamber 24 in the form of a liquid or gel 30. The fluid 30 surrounds the osmotic tablet 26, fills the spaces between the osmotic tablet and the chamber walls and displaces substantially all air or gas within the second chamber, but does not cause the osmotic tablet to swell and freeze-up.

In the embodiment described above, machining and tableting tolerances require that there be an annular gap between the osmotic tablet 26 or tablets and the surrounding capsule side walls. Small irregularities in the shape or contour of the tablet 26 may also result in a gap between the osmotic tablet and the movable piston 22, and/or between the osmotic tablet and the membrane plug 28. These gaps which are filled with air in the known drug delivery systems will vary in size from, for example, between approximately 0.001 to 0.1 inches. Even the smallest of gaps can cause a delay of several days to weeks before the delivery system begins to deliver the beneficial agent. Additionally, air-filled gaps problematically affect the beneficial agent delivery rate when an osmotic delivery system is subjected to different external pressures, such as when a patient with an implanted device scuba dives or travels to higher altitudes.

The fluid 30 which is provided within the second chamber 24 according to the present invention displaces the air surrounding the osmotic tablet and improves start-up time, which is the time from insertion of the device into the fluid environment of use until the beneficial agent is actually delivered at a rate preferably not less than approximately 70% of the intended steady-state or pulsating rate. For example, the time to reach full delivery with a one year implantable osmotic drug delivery system that does not use a fluid additive 30 according to the present invention is about 30 days. Use of a fluid filler or additive 30 according to the present invention shortens that period to less than about 15 days.

The fluid 30 is preferably an incompressible fluid which does not compress upon swelling of the osmotic tablet. The incompressible fluid 30 reduces the start-up time for the osmotic drug delivery device 10 because the delay during which the osmotic tablet swells to fill the surrounding air space of the known devices is eliminated. Furthermore, if the osmotic activity of the fluid 30 is selectively higher than that of the osmotic agent or tablet 26, the addition of the fluid 30 may further increase the initial and/or steady state delivery rate of the beneficial agent. In general, the incompressible fluid additive 30 may be any liquid that is acceptable for human implantation.

Figure 2:
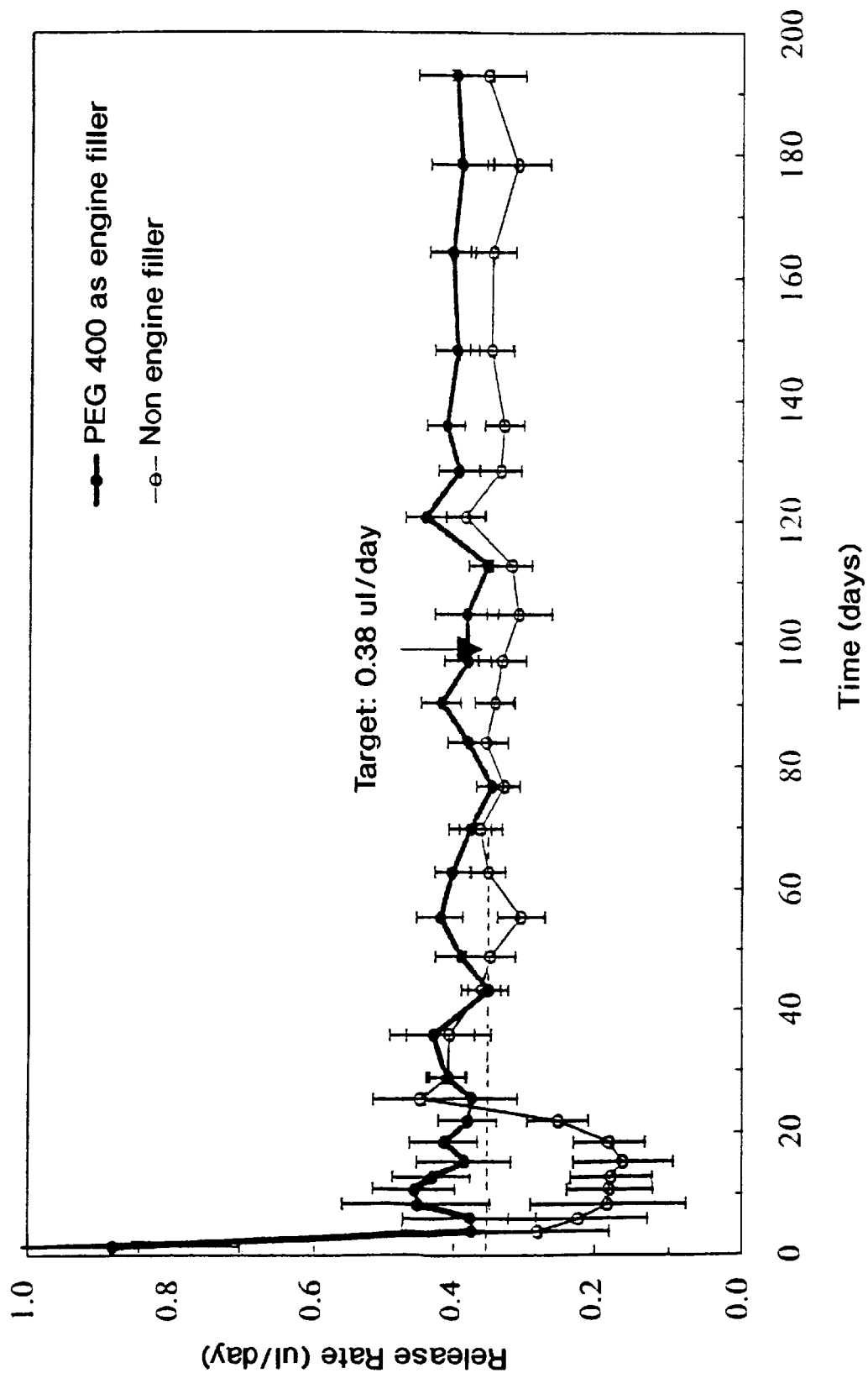
FIG. 2 is a graph illustrating the improved release rate of an osmotic delivery device according to the present invention.

FIG. 2 illustrates the effect of the fluid additive 30 on the delivery of the beneficial agent. FIG. 2 is a graph of the release rate over time comparing one example of a delivery system according to the present invention with a delivery system without a fluid additive. As shown in FIG. 2 the release rate of an osmotic delivery system without an additive does not achieve the desired substantially constant delivery rate of approximately 0.38 uL/day until about 35 days after placing the capsule in the agent delivery environment. This 35 day time period for the desired delivery rate to be achieved is the start-up period. In contrast, the start-up period is substantially eliminated for an embodiment of the present invention which includes a fluid additive or osmotic engine filler (PEG 400); the system takes only about 5 to 10 days to reach the desired substantially constant delivery rate. In addition, the beneficial agent delivery rate according to an embodiment of the present invention, which includes the fluid additive 30, is more consistent throughout the entire agent delivery period than the delivery rate of a system without the fluid additive.

Furthermore, the beneficial agent delivery rate of an embodiment of the present invention such as that illustrated in FIG. 1 is not affected by external pressure changes of approximately +/−0.5 atmospheres.

For a total test period of 190 days, the example of the present invention illustrated in FIG. 2 has a start-up time of less than 10%, preferably less than 7%, of the total administration period; the total administration period for the embodiment of the present invention tested in FIG. 2 was one year. Although the test period for the embodiment of the present invention tested in FIG. 2 was 190 days, and the total administration period was 365 days, both may differ. The administration period is typically predetermined and depends upon the particular application; for example, the administration period is at least about one day, sometimes greater than 7 days, often between about 30 days and 2 years, preferably greater than about 1 month, and usually between about 1 month and 12 months.

Figure 3:
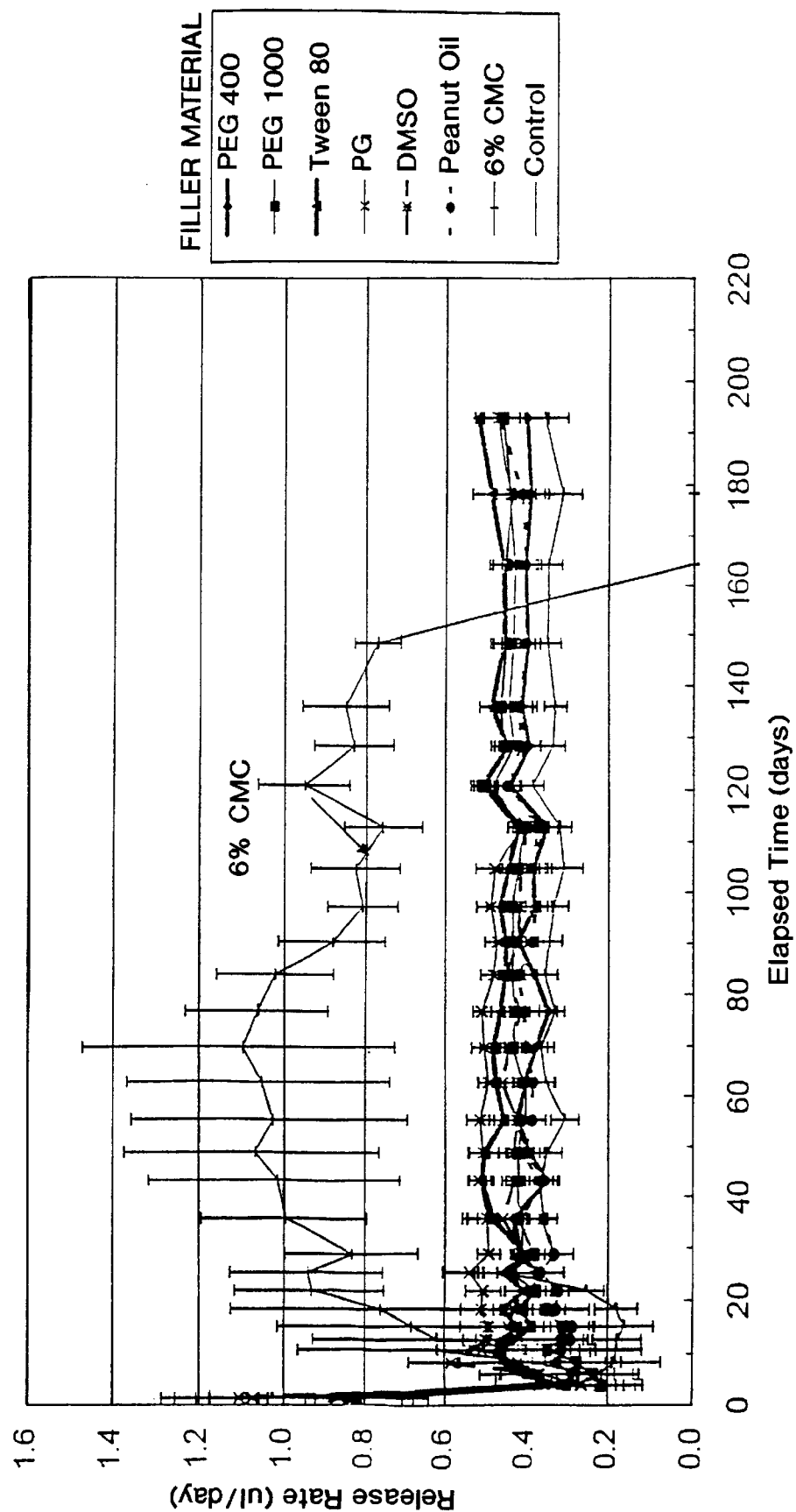
FIG. 3 is a graph illustrating the resulting improved release rates corresponding to different embodiments of the present invention which each include a different fluid additive.

FIG. 3 illustrates the effect of different fluid additives 30 on the delivery of the beneficial agent. FIG. 3 is a graph of the release rate over time comparing seven embodiments of osmotic delivery systems according to the present invention, six of which each include a fluid additive which is not significantly absorbed by the osmotic agent (PEG 400, PEG 1000, Tween 80, PG, DMSO, and peanut oil), and one of which includes a fluid additive which is absorbed by the osmotic agent (6% CMC in water). The release rates over time for the seven embodiments are compared to a delivery system without a fluid additive (control).

As shown in FIG. 3, the start-up time for the control system is about 35 days, and is about 5 to 10 days for the embodiments of the present invention which includes a fluid additive. FIG. 3 also illustrates that the release rate may be selectively increased by using a predetermined fluid additive 30. For example, the average release rate for an embodiment of the present invention including the Tween 80 additive is approximately 0.3 uL/day higher than that of an embodiment of the present invention including the PEG 400 additive.

Furthermore, FIG. 3 illustrates that by using additives such as 6% CMC in water, which is absorbed by the osmotic agent and leaves a lubricating film on the exterior of the agent, the release rate may be dramatically increased while also substantially eliminating the start-up period.

In addition to greatly improving the start-up period, the fluid 30 surrounding the osmotic tablet 26 also acts as a lubricant to prevent the osmotic tablet 26 from locking against the capsule side walls during initial wetting of the tablet. The locking of the osmotic tablet 26 against the capsule side walls creates substantial problems including freezing-up of the osmotic agent and pumping rate for a period of time necessary to soften the tablet to a state at which it can flow. This problem is particularly dramatic when the predetermined administration period must be short in order to quickly deliver the beneficial agent. Locking of the osmotic tablet 26 may also cause the membrane plug 28 to be dislodged or to rupture, and may cause rupture of the capsule itself. In order to avoid these problems, a fluid filler or additive 30 is preferably selected to surround and lubricate the osmotic tablet 26.

The fluid 30 which surrounds the osmotic tablet 26 in the osmotic drug delivery system according to the present invention may be either a liquid or a gel. The fluid 30 is preferably selected to be either a fluid which is not significantly absorbed by the osmotic tablet, such as low molecular weight PEG's, perfluorodecalin, Tween 80, Tween 20, PG, DMSO, or peanut oil. The fluid additive 30 may also be a fluid which is absorbed by the osmotic tablet, leaves a lubricating film on the exterior of the osmotic tablet, and prevents the system from freezing-up, such as carboxymethyl cellulose/water gels.

The fluid 30 should not diffuse out of the system during normal storage. In addition, the fluid 30 should be acceptable as an unharmful parenteral excipient which could be delivered to the body in the event the capsule ruptures or breaks and the fluid in the engine is exposed.

The fluid 30 should also be a fluid which does not diffuse out through the membrane plug 28 during storage or react with the membrane plug, piston, or the capsule itself. The fluid 30 is also selected so that contact with the fluid does not change the permeability of the membrane plug.

Acceptable additives or fillers for use in the present invention include but are not limited to polymers, such as polyethylene glycol (PEG) 400 and PEG 1000, propylene glycol (PG), polyoxyethylene sorbitan monolaurate (Tween 20), polyoxyethylene sorbitan monooleate (Tween 80), dimethyl sulfoxide (DMSO), perfluorodecalin, silicone oils, organic liquids, and water or saline (if used with a properly selected osmotic agent, such as 100% NaCl). The fluid additive or filler may also be a gel, such as 6% carboxymethyl cellulose (CMC) in water.

Among the additives tested, the additives which resulted in engine freeze-up include saturated NaCl solution, 1% CMC in water, water, 30% Tween 20 in saline, and hydroxypropyl methylcellulose (HPMC) when used with the osmotic tablet described below. For testing purposes, engine freeze-up occurred when greater than 100 psi was needed to move the osmotic tablet. However, lower pressures may be indicative of problematic freeze-ups during actual use of the osmotic delivery systems. Although the above-described fluids were found to result in osmotic engine freeze-up in the particular system tested, they may be useful in the present invention with osmotic agents other than the one tested. The osmotic agent used in the above described tests was a salt tablet with a gellant, more particularly, a salt tablet with 79.6% NaCl, 12.2% NaCMC, 5.9% Plasdone, 1.7% $H_2O$, and 0.5% Mg stearate. In general, any combination of osmotic agent and fluid additives which are inert with the membrane, piston, and capsule may be used as long as the osmotic agent does not cause swelling which leads to osmotic agent freeze-up within the capsule, which is easily determined from experimentation.

Materials which may be used for the capsule 12 must be sufficiently strong to ensure that the capsule will not leak, crack, break, or distort under stresses to which it would be subjected during implantation or under stresses due to the pressures generated during operation. The capsule 12 may be formed of chemically inert and biocompatible, natural or synthetic materials which are known in the art. The capsule material is preferably a non-bioerodible material which remains in the patient after use, such as titanium. However, the material of the capsule may alternatively be of bioerodible material which bioerodes in the environment after dispensing of the beneficial agent. Generally, preferred materials for the enclosure or capsule 12 are those acceptable for human implants.

In general, typical materials of construction suitable for the capsule 12 according to the present invention include non-reactive polymers or biocompatible metals or alloys. The polymers include acrylonitrile polymers such as acrylonitrile-butadiene-styrene terpolymer, and the like; halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the capsule 12 include stainless steel, titanium, platinum, tantalum, gold, and their alloys, as well as gold-plated ferrous alloys, platinum-plated ferrous alloys, cobalt-chromium alloys and titanium nitride coated stainless steel.

In general, materials suitable for use in the piston 22 are elastomeric materials including the non-reactive polymers listed above, as well as elastomers in general, such as polyurethanes and polyamides, chlorinated rubbers, styrene-butadiene rubbers, and chloroprene rubbers.

The osmotic tablet 26 is an osmotic agent which is a fluid-attracting agent used to drive the flow of the beneficial agent. The osmotic agent may be an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross linked with glyoxal, formaldehyde or glutaraldehyde and having a degree of polymerization of 200 to 30,000, a mixture of methyl cellulose, cross linked agar and carboxymethylcellulose, a mixture of hydroxypropl methycellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross linked indene-maleic anhydride polymers, Good-Rite polyacrylic acids having molecular weights of 80,000 to 200,000, Polyox Polyethylene oxide polymers having molecular weights of 100,000 to 5,000,000, starch graft copolymers, and Aqua-Keeps acrylate polymer polysaccharides.

Delivery capsules in accordance with the present invention for the delivery of beneficial agents, may be manufactured by a variety of techniques, many of which are known in the art. In one such technique, the beneficial agent and an osmotically active agent are prepared as solid or semi-solid formulations and pressed into pellets or tablets whose dimensions correspond to slightly less than the internal dimensions of the respective chambers which they will occupy in the capsule interior. Depending on the nature of the materials used, the two agents and other solid ingredients which may be included with them may be processed prior to the formation of the pellets by such procedures as ballmilling, calendaring, stirring or rollmilling to achieve a fine particle size and hence fairly uniform mixtures of each. The capsule may be formed from any of the wall-forming materials disclosed above by the use of a mold, with the materials applied either over the mold or inside the mold, depending on the mold configuration. In assembling the osmotic delivery device according to one embodiment of the present invention, the piston 22 is first inserted into the capsule 12. Thereafter, a filler tip of a micro pipet or similar dispenser well known in the art is inserted into the capsule to dispense the fluid additive 30. Then an osmotic agent 26 is placed in the capsule 12; specifically, once the osmotic pellets or tablets have been formed, they are placed inside the pre-formed capsule with the piston or partion 22. Where an end cap or membrane plug 28 is a part of the device, such is then placed onto the capsule to close it. Finally, the beneficial agent is inserted into the end of the capsule opposite the plug 28.

The capsule orifice 18 or orifices are also formed by conventional techniques which are known in the art. Included among these methods are mechanical drilling, laser drilling, and molding. The capsule will contain at least one such orifice, and in most configurations, one orifice will suffice. However, two or more orifices may be present without departing from the present invention. The dimensions of the orifice in terms of both diameter and length will vary with the type of beneficial agent, the rate at which the beneficial agent is to be delivered, and the environment into which it is to be delivered. The considerations involved in determining the optimum dimensions of the orifice for any particular capsule or beneficial agent are the same as those for orifices of capsules of the prior art, and selection of the appropriate dimensions will be readily apparent to those skilled in the art.

In other embodiments of this invention, the beneficial agents contained in the first chamber 20 are flowable compositions such as liquids, suspension, or slurries, and are poured into the capsule after the osmotic agent and the piston 22 have been inserted. Still further alternatives may include any of the wide variety of techniques known in the art for forming capsules used in the pharmaceutical industry.

Animals to whom drugs may be administered using systems of this invention include humans and other animals.

The invention is of particular interest for application to humans and household, sport, and farm animals, particularly mammals. For the administration of beneficial agents to animals, the devices of the present invention may be implanted subcutaneously or intraperitoneally wherein aqueous body fluids are available to activate the osmotic engine. Devices of the invention may also be administered to the rumen of ruminant animals, in which embodiment the devices may further comprise a density element for maintaining the device in the rumen for extended periods of time of up to 120 days or longer. Density elements are well known in the art of drug delivery devices.

The devices of this invention are also useful in environments outside of physiological or aqueous environments. For example, the devices may be used in intravenous systems (attached to an IV pump or bag or to an IV bottle, for example) for delivering beneficial agents to animals, primarily to humans. They may also be utilized in blood oxygenators, kidney dialysis and electrophoresis, for example. Additionally, devices of the present invention may be used in the biotechnology area, such as to deliver nutrients or growth regulating compounds to cell cultures. In such instances, activating mechanisms such as mechanical mechanisms are particularly useful.

The present invention applies to the administration of beneficial agents in general, which include any physiologically or pharmacologically active substance. The beneficial agent may be any of the agents which are known to be delivered to the body of a human or an animal such as medicaments, vitamins, nutrients, or the like. The beneficial agent may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phemnetrazine hydrochloride, bethanechol chloride, methacholine chloride, pilocarpine hydrochloride, atropine sulfate, scopolamine bromide, isopropamide iodide, tridihexethyl chloride, phenfornin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagultion factors, human pancreas hormone releasing factor, analogs and derivatives of these compounds, and pharmaceutically acceptable salts of these compounds, or their analogs or derivatives.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations may be used. Derivatives such as esters, ethers and amides can also be used. An active agent can be used alone or mixed with other active agents.

According to other embodiments of the present invention, the capsule 12 may take different forms. For example the membrane plug 28 may be eliminated and the walls of the second chamber 24 itself may be formed of a membrane material. The fluid delivery orifice 18 may be a soft impermeable material. In addition, the piston 22 may be replaced with a flexible member such as a diaphragm, partition, pad, flat sheet, spheroid, or rigid metal alloy, and may be made of any number of inert materials. Furthermore, the osmotic device may function without the piston 22, having simply an interface between the osmotic agent/fluid additive and the beneficial agent.

While the invention has been described in detail with reference to a preferred embodiment thereof, it will be apparent to one skilled in the art that various changes can be made, and equivalents employed without departing from the spirit and scope of the invention.

What is claimed is:

1. An osmotic drug delivery device comprising:
    a capsule including a first chamber containing a beneficial agent and a second chamber containing an osmotic agent, said first chamber having an opening through which the beneficial agent may be delivered from the first chamber to a location external of the first chamber;
    a movable separating member positioned in the capsule between the first chamber and the second chamber;
    a wall of the second chamber including a fluid permeable portion allowing fluid to pass from a surrounding environment into the second chamber; and
    an incompressible fluid additive located within the second chamber and substantially surrounding the osmotic agent.

2. The osmotic drug delivery system according to claim 1, wherein the osmotic agent is in a tabular form and the fluid additive surrounds the tabular osmotic agent.

3. The osmotic drug delivery system according to claim 1, wherein the separating member is a slidable piston.

4. The osmotic drug delivery device according to claim 1, wherein the fluid permeable portion is a membrane.

5. The osmotic drug delivery device according to claim 1, wherein the osmotic agent is a tablet.

6. The osmotic drug delivery device according to claim 1, wherein the fluid additive is a lubricating liquid for preventing freeze-up of the osmotic agent.

7. The osmotic drug delivery device according to claim 1, wherein the fluid additive is a gel.

8. The osmotic drug delivery device according to claim 1, wherein the fluid additive includes PEG.

9. The osmotic drug delivery system according to claim 1, including at least one gap between an inner surface of the capsule and the osmotic agent, said fluid additive filling the at least one gap to improve start-up time.

10. The osmotic drug delivery system according to claim 1, wherein the osmotic agent includes NaCl and the fluid additive includes PEG.

11. An osmotic drug delivery device comprising:
    an enclosure holding at least one osmotic agent tablet which imbibes fluid from a surrounding environment and swells to cause delivery of a beneficial agent; and
    an incompressible fluid filler located within the enclosure and at least partially surrounding the osmotic agent tablet.

12. The osmotic drug delivery system according to claim 11, wherein the fluid filler is an osmotic agent.

13. The osmotic drug delivery system according to claim 11, wherein the osmotic agent is a fluid swellable material causing delivery of the beneficial agent at a controlled rate.

14. The osmotic drug delivery device according to claim 11, wherein the fluid filler is a lubricating liquid.

15. The osmotic drug delivery device according to claim 11, wherein the fluid filler is a gel.

16. The osmotic drug delivery device according to claim 11, wherein the fluid filler is PEG 400.

17. The osmotic drug delivery system according to claim 11, including at least one gap between an inner surface of the enclosure and an exterior surface of the osmotic agent tablet, the fluid filler filling the at least one gap.

18. The osmotic drug delivery device according to claim 11, wherein the enclosure includes a first chamber for containing the beneficial agent and a second chamber, the second chamber containing the osmotic agent tablet and the fluid filler.

19. The osmotic drug delivery device according to claim 18, wherein the first chamber and the second chamber are separated by a partition.

20. The osmotic drug delivery system according to claim 19, wherein the partition is a slidable piston.

21. A method of improving start-up time of an osmotic drug delivery system that includes an enclosure, an osmotic agent tablet provided within the enclosure, and a gap between an inner surface of the enclosure and an outer surface of the osmotic agent tablet, comprising the step of removing gas between the outer surface of the osmotic agent tablet and the inner surface of the enclosure by providing an incompressible fluid in the gap.

22. An osmotic drug delivery device comprising:
    an enclosure;
    a partition dividing the enclosure so as to define a first chamber located on a first side of the partition and a second chamber located on a second side of the partition opposite from the first side, the first chamber holding a beneficial agent and the second chamber holding an osmotic agent, a portion of the enclosure that defines the first chamber being substantially impermeable to fluids, another portion of the enclosure that defines at least a part of the second chamber being permeable to fluids, the osmotic agent for imbibing fluid from a surrounding environment through said another portion of the enclosure and for swelling to cause delivery of the beneficial agent; and
    an incompressible fluid filler located within the second chamber and at least partially surrounding the osmotic agent.

23. The osmotic drug delivery device of claim 22, wherein the partition includes a movable piston, the osmotic agent includes a tablet, and the first chamber includes a delivery orifice through which the beneficial agent may be delivered from the first chamber to a location external of the delivery device.

* * * * *